United States Patent [19]

Grivsky

[11] 4,107,320
[45] Aug. 15, 1978

[54] BIOLOGICALLY ACTIVE AMIDES
[75] Inventor: Eugene Michael Grivsky, Chapel Hill, N.C.
[73] Assignee: Burroughs Wellcome Co., Research Triangle Park, N.C.
[21] Appl. No.: 712,133
[22] Filed: Aug. 6, 1976
[51] Int. Cl.² ............ A61K 31/33; A61K 31/40; A61K 31/445
[52] U.S. Cl. .................... 424/274; 424/244; 424/267
[58] Field of Search ............ 424/274, 267, 244; 260/240

[56] References Cited
U.S. PATENT DOCUMENTS

| 3,488,749 | 1/1970 | Loev | 424/324 |
|---|---|---|---|
| 3,590,041 | 6/1975 | Kleemann | 260/240 |
| 3,780,102 | 12/1973 | Baipsot | 424/324 |
| 4,041,071 | 8/1977 | Grivsky | 424/324 |

FOREIGN PATENT DOCUMENTS 1,396,941   6/1975   United Kingdom.
1,396,942   6/1975   United Kingdom.

OTHER PUBLICATIONS

Chim. Ther. (1967), 2 (5), 354–365.
Bulletin de la Societe Chimique de France, 1969, No. 11, 3802–3806.

Primary Examiner—Stanley J. Friedman
Attorney, Agent, or Firm—Donald Brown

[57] ABSTRACT

Compounds of formula (I),

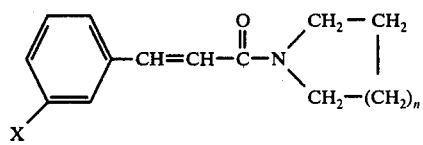

wherein X is hydrogen, fluoro, chloro, bromo, iodo, trifluoromethyl, alkyl or alkoxy and n is 1 to 4, have anticonvulsant properties.

10 Claims, No Drawings

BIOLOGICALLY ACTIVE AMIDES

This invention is concerned with chemicals which have valuable pharmacological properties. In particular, the invention concerns cinnamamides, their synthesis, pharmaceutical preparations containing them, and their use in medicine.

It has been found that the cinnamamides of formula (I), as defined below, have anti-convulsant activity in mammals as is shown by their effects upon mice when administered to them in established pharmacological tests. These tests are:

1. Maximal Electroshock Test (MES) in mice, a method described by Woodbury and Davenport, Arch int. Pharmacodyn. Ther. 92. P. 97–107 (1952).
2. Metrazol Seizure Test (MET) in mice, a method described by Swinyard, Brown and Goodman, J. Pharmacol. Exp. Therap. 106, 319–330 (1952).

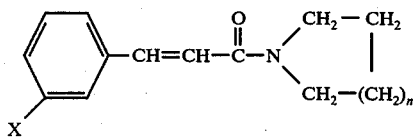

X is hydrogen, fluoro, chloro, bromo, iodo, trifluoromethyl, alkyl having 1 to 4 carbon atoms or alkoxy having 1 to 4 carbon atoms in the alkyl moiety thereof; and n is an integer from 1 to 4. The trans configuration of the compounds of formula (I) is preferred.

The compound 1-(3-chlorocinnamoyl)pyrrolidine has been found to have particularly valuable anti-convulsant properties as demonstrated in the above-mentioned pharmacoligical tests.

The compounds of formula (I) may be made by any method known for the synthesis of cinnamamides of analogous structure. For example they may be prepared by the acylation of an amine of formula (II),

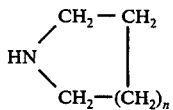

wherein n is an integer from 1 to 4, by the corresponding acid of formula (III), 3—X—PhCH=CHCO₂H (wherein X has the same meaning as in formula (I)) or a reactive derivative thereof such as a thioester or an ester (eg. an alkyl ester or thioester where the alkyl has eg. 1 to 4 carbon atoms), an amide, an acid halide (eg. an acid chloride) or an acid anhydride. A wide variety of reaction conditions may be employed depending upon the nature of the acylating agent, but in general the reactants may be refluxed together, preferably in an inert liquid medium such as ether, benzene, toluene or cyclohexane.

A most convenient method of synthesis is to react the acid chloride with the appropriate amine. Preferably one equivalent of the halide should be used with two or more equivalents of the amine, but the molar excess of the amine may be replaced by another base such as triethylamine, pyridine, dimethylaniline, or potassium or sodium carbonate. A wide variety of polar or non-polar liquid media may be used including water, alkanols such as methanol, ethanol, etc., ether, dioxane, benzene, toluene, xylene, petroleum ether, cyclohexane, tetrahydrofuran, chloroform and carbon tetrachloride. A wide range of temperature conditions may be employed, for example from −10° C. to the reflux temperature of the reaction mixture.

The compounds of formula (I) may be further prepared directly from the corresponding alcohol or aldehyde of formula (IV) and (V) at a temperature below 10° C.

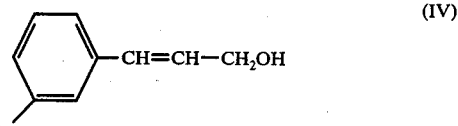

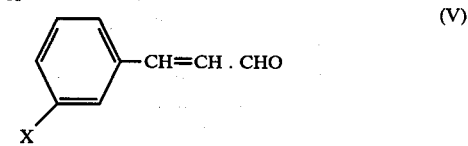

wherein X has the meaning in formula (I), by reaction with an appropriate amine of formula (II) in the presence of nickel peroxide and an inert liquid medium such as ether, benzene, tetrahydrofuran, or a petroleum hydrocarbon.

In a further method for making a compound of formula (I), water, a hydrogen halide or molecular halogen is eliminated from a compound of formula (VI)

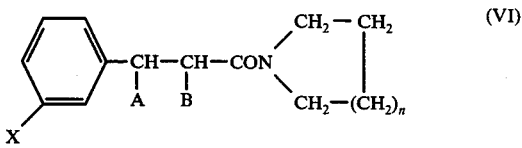

wherein A and B are the same and each is halo or one of A and B is halo or hydroxy and the other is hydrogen, and X and n have the meaning given in formula (I) above. For example, the elimination of water from the α- or β-hydroxy compounds of formula (VI) may be effected by reaction with a dehydrating agent such as a base (eg. aqueous sodium hydroxide) or concentrated sulphuric or polyphosphoric acid. The monohalo intermediates may be treated with a base (eg. potassium hydroxide or dimethylaniline) or merely heated to release the hydrogen halide. The di-halo intermediates may be reduced, for example with zinc and ethanol or converted to the diiodo compounds by treatment with potassium iodide with subsequent release of molecular iodine.

The intermediate acids of formula (III) may be made by classical organic synthetic methods such as the Perkin synthesis, the Reformatsky reaction and the Knoevenagel condensation.

The compounds of formula (I) may be used for the treatment or prophylaxis of convulsions of mammals such as mice, dogs and cats, and more importantly of man. In particular they may be used in the treatment of grand mal, petit mal, psychomotor epilepsy and focal seizures at a dose of 2 to 200 mg/kg of body weight per day. The optimum dose of course will vary with the nature of the compound, the condition of the patient and the route of administration, but the preferred dose is in the range of 20 to 60 mg/kg, most conveniently 30 to 50 mg/kg body weight, per day. Administration of the desired daily dose is preferably in three divided doses.

For example, convenient forms of administration include tablets each containing from 100 to 500 mg of a compound of formula (I).

For use in medicine the compounds of formula (I) may be administered as a pure chemical but are preferably presented with an acceptable carrier therefor as a pharmaceutical composition. The carrier must of course be 'acceptable' in the sense of being compatible with the other ingredients of the composition and not deleterious to the recipient of the composition. The carrier may be a solid or a liquid or a mixture of solid and liquid substances, and is preferably formulated with a compound of formula (I) as a unit-dose composition, for example a tablet, capsule or sachet for oral administration or a suppository for rectal administration. Other pharmaceutically active substances may also be present in compositions of the present invention, and the composition may be formulated by any of the well-known techniques of pharmacy consisting basically of admixture of its components. Unit-dose compositions, for oral, rectal or parenteral administration (vid. inf.), conveniently contain a compound of formula (I) in an amount in the range 100 to 500 mg.

For oral administration, fine powders or granules of the compounds may contain diluents and dispersing and surface active agents, and may be presented in a draught in water or in a syrup; in capsules or cachets in the dry state or in an aqueous or non-aqueous suspension, when a suspending agent may also be included; in tablets, preferably made from granules of the active ingredient with a diluent, by compression with binders and lubricants; or in a suspension in water or a syrup or an oil or in a water/oil emulsion, when flavouring, preserving, suspending, thickening and emulsifying agents may also be included. The granules or the tablets may be coated, and the tablets may be scored.

For parenteral administration (by intramuscular or intraperitoneal injection), the compounds may be presented in unit dose or multi-dose containers in aqueous or non-aqueous injection solutions which may contain antioxidants, buffers, bacteriostats and solutes which render the compounds isotonic with the blood; or in aqueous or non-aqueous suspensions when suspending agents and thickening agents may also be included; extemporaneous injection solutions and suspensions may be made from sterile powders, granules or tablets which may contain diluents, dispersing and surface active agents, binders and lubricants.

It will be understood from the foregoing description that what we will claim in accordance with this invention comprises any novel feature described herein, principally but not exclusively as follows:
(a) Any novel compound of formula (I)
(b) A compound of formula (I) wherein $n$ is 1
(c) A compound of formula (I) wherein $n$ is 2
(d) A compound of formula (I) wherein $n$ is 3
(e) A compound of formula (I) wherein $n$ is 4
(f) A compound of formula (I) wherein X is fluoro, chloro, bromo, iodo or trifluoromethyl.
(g) A compound of the formula (I) having the trans configuration
(h) 1-(3-Chlorocinnamoyl)pyrrolidine
(i) The synthesis of a compound of formula (I) by any known method and in particular the methods specifically described above and including the reaction of an acid m-X-PhCH=CHCO$_2$H or a reactive derivative thereof with an amine of the formula (II) as hereinbefore defined.
(j) A pharmaceutical composition comprising a compound of formula (I) and a pharmaceutically acceptable carrier therefor.
(k) A method for the treatment or prophylaxis of convulsions of a mammal comprising the administration to the mammal of an anti-convulsant effective, non-toxic amount of a compound of formula (I).

The following Examples illustrate the present invention but should not be construed as in any way constituting a limitation thereof. All temperatures are in degrees Celsius.

EXAMPLE 1 Trans-1-(3-chlorocinnamoyl)pyrrolidine

A solution of trans-3-chlorocinnamic acid (25.5 g) and thionyl chloride (33.6 g) in dry benzene (300 ml) was heated at reflux until the evolution of HCl and SO$_2$ had ceased. Excess thionyl chloride and benzene were removed by distillation under reduced pressure to give trans-3-chlorocinnamoyl chloride (28 g) as an oil. A solution of trans-3-cinnamoyl chloride (4.0 g) in dry toluene (75 ml) was added with stirring to a solution of pyrrolidine (4.3 g) in dry benzene (75 ml) at ambient temperature. The reaction mixture was allowed to stir for 10 hr., after which time excess pyrrolidine and solvents were removed under reduced pressure. The residue was triturated with water, filtered, and recrystallized from ethanol/water as follows: the wet solid was dissolved in warm (40 – 45° C) ethanol (90 ml), the resulting solution filtered, and water (ca. 900 ml) added giving crystalline trans-1-(3-chlorocinnamoyl)pyrrolidine, m.p. 137 – 138° C. Elemental analysis, NMR, and IR spectra are consistent with the assigned structure.

EXAMPLE 2

A suppository was formulated from the following ingredients:
trans 1-(3-chlorocinnamoyl)pyrrolidine — 300 mg
cocoa butter — 2000 mg

EXAMPLE 3

A soft gelatin capsule was filled with the following ingredients:
trans 1-(3-chlorocinnamoyl)pyrrolidine — 300 mg
lactose — 75 mg
starch, corn — 20 mg
fused silica — 2 mg
magnesium stearate — 3 mg

EXAMPLE 4

A syrup suspension was prepared from the following ingredients:
trans 1-(3-chlorocinnamoyl)pyrrolidine — 300 mg
sodium carboxymethylcellulose — 20 mg
microcrystalline cellulose — 100 mg
glycerin — 500 mg
Polysorbate 80 — 10 ml
flavouring agent — q.s.
preserving agent — 0.1%
sucrose syrup — q.s. to 5 ml

EXAMPLE 5

A compressed tablet was prepared from the following:
trans 1-(3-chlorocinnamoyl)pyrrolidine — 300 mg
starch, corn — 50 mg
microcrystalline cellulose — 50 mg
stearic acid — 4 mg
magnesium stearate — 1 mg fused silica — 1 mg

EXAMPLE 6

In the MES and MET pharmacological tests referred to hereinbefore, trans 1-(3-chlorocinnamoyl)pyrrolidine had an $ED_{50}$ (i.p.) in rats of 52 mg/kg and 38 mg/kg respectively.

What I claim is:

1. A method of treatment or prophylaxis of convulsions in a mammal susceptible to convulsions because of a previous occurrence of convulsions comprising the administration to said mammal of an anticonvulsant effective, non-toxic amount of a compound of formula (I)

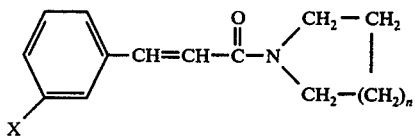

wherein X is selected from the group consisting of hydrogen, fluoro, chloro, bromo, iodo, trifluoromethyl, alkyl having 1 to 4 carbon atoms and alkoxy having 1 to 4 carbon atoms in the alkyl moiety thereof; and n is an integer from 1 to 4.

2. The method as claimed in claim 1 wherein the compound of formula (I) has the trans configuration.

3. The method as claimed in claim 1 wherein in formula (I) n is 1 or 2.

4. The method as claimed in claim 1 wherein in formula (I) X is selected from the group consisting of fluoro, chloro, bromo, iodo and trifluoromethyl.

5. The method as claimed in claim 2 wherein the compound of formula (I) is 1-(3-chlorocinnamoyl)pyrrolidine.

6. The method as claimed in claim 1 wherein the mammal is man.

7. The method as claimed in claim 1 wherein the convulsions are selected from grand mal, petit mal, psychomotor epilepsy and focal seizures.

8. The method as claimed in claim 1 wherein the compound is administered by the oral route.

9. The method as claimed in claim 1 wherein the compound is administered at a dose of 2 to 200 mg/kg mammal body weight per day.

10. The method of claim 1 wherein the compound is trans-1-(3-chlorocinnamoyl)pyrrolidine.

* * * * *